United States Patent
Königsmann et al.

(10) Patent No.: US 9,084,983 B2
(45) Date of Patent: Jul. 21, 2015

(54) CATALYST AND PROCESS FOR HYDROGENATING AROMATICS

(75) Inventors: Lucia Königsmann, Stuttgart (DE); Daniela Mirk, Speyer (DE); Thomas Heidemann, Viernheim (DE); Michael Hesse, Worms (DE); Martin Bock, Mannheim (DE); Mario Emmeluth, Bensheim (DE); Jutta Bickelhaupt, Fränkisch-Crumbach (DE)

(73) Assignee: BASF SE (DE)

( * ) Notice: Subject to any disclaimer, the term of this patent is extended or adjusted under 35 U.S.C. 154(b) by 330 days.

(21) Appl. No.: 13/516,124

(22) PCT Filed: Dec. 14, 2010

(86) PCT No.: PCT/EP2010/069637
§ 371 (c)(1),
(2), (4) Date: Jun. 14, 2012

(87) PCT Pub. No.: WO2011/082991
PCT Pub. Date: Jul. 14, 2011

(65) Prior Publication Data
US 2012/0296111 A1 Nov. 22, 2012

(30) Foreign Application Priority Data
Dec. 15, 2009 (EP) .................................. 09179201

(51) Int. Cl.
| | | |
|---|---|---|
| C07C 69/74 | (2006.01) |
| C07C 61/00 | (2006.01) |
| C07C 209/00 | (2006.01) |
| C07C 31/13 | (2006.01) |
| C07C 29/00 | (2006.01) |
| C07C 5/10 | (2006.01) |
| B01J 21/00 | (2006.01) |
| B01J 23/40 | (2006.01) |
| B01J 21/08 | (2006.01) |
| B01J 23/46 | (2006.01) |
| B01J 35/00 | (2006.01) |
| B01J 35/10 | (2006.01) |
| B01J 37/02 | (2006.01) |
| C07C 29/20 | (2006.01) |
| C07C 51/36 | (2006.01) |
| C07C 67/303 | (2006.01) |
| C07C 209/72 | (2006.01) |

(52) U.S. Cl.
CPC *B01J 23/40* (2013.01); *B01J 21/08* (2013.01); *B01J 23/462* (2013.01); *B01J 35/008* (2013.01); *B01J 35/0026* (2013.01); *B01J 35/0053* (2013.01); *B01J 35/108* (2013.01); *B01J 35/1019* (2013.01); *B01J 35/1042* (2013.01); *B01J 35/1061* (2013.01); *B01J 37/0201* (2013.01); *B01J 37/0203* (2013.01); *B01J 37/0205* (2013.01); *C07C 5/10* (2013.01); *C07C 29/20* (2013.01); *C07C 51/36* (2013.01); *C07C 67/303* (2013.01); *C07C 209/72* (2013.01); *C07C 2101/14* (2013.01); *C07C 2521/08* (2013.01); *C07C 2523/46* (2013.01)

(58) Field of Classification Search
USPC .................. 502/261, 262; 560/127; 562/511; 564/450, 451; 568/831, 835; 585/269
See application file for complete search history.

(56) References Cited

U.S. PATENT DOCUMENTS

| | | | |
|---|---|---|---|
| 2,757,128 A | 7/1956 | Hemminger | |
| 3,161,605 A * | 12/1964 | Stiles et al. .................... | 502/243 |
| 3,245,919 A | 4/1966 | Gring et al. | |
| 3,753,926 A | 8/1973 | Hayes | |
| 3,851,004 A | 11/1974 | Yang | |
| 4,072,628 A | 2/1978 | Kruse et al. | |
| 4,218,308 A * | 8/1980 | Itoh et al. ....................... | 502/261 |
| 4,452,951 A | 6/1984 | Kubo et al. | |
| 4,497,909 A * | 2/1985 | Itoh et al. ...................... | 502/262 |
| 5,110,779 A * | 5/1992 | Hucul ............................ | 502/185 |
| 5,495,055 A | 2/1996 | Rueter | |
| 5,849,972 A | 12/1998 | Vicari et al. | |
| 5,879,539 A * | 3/1999 | Mignard et al. ............... | 208/138 |
| 6,248,924 B1 | 6/2001 | Ruhl et al. | |
| 6,284,917 B1 | 9/2001 | Brunner et al. | |
| 6,603,038 B1 | 8/2003 | Hagemeyer et al. | |
| 7,256,153 B2 * | 8/2007 | Frenzel et al. ................ | 502/243 |
| 7,270,738 B2 * | 9/2007 | Euzen et al. ................. | 208/111.3 |
| 7,452,844 B2 * | 11/2008 | Hu et al. ....................... | 502/327 |
| 7,563,743 B2 * | 7/2009 | Euzen et al. .................. | 502/208 |
| 7,585,812 B2 * | 9/2009 | Hu et al. ....................... | 502/327 |
| 7,745,370 B2 * | 6/2010 | Blankenship et al. ........ | 502/262 |
| 8,455,389 B2 * | 6/2013 | Liwanga-Ehumbu et al. .............................. | 502/261 |
| 2003/0009051 A1 | 1/2003 | Bohnen et al. | |

(Continued)

FOREIGN PATENT DOCUMENTS

| | | |
|---|---|---|
| BE | 882279 A1 | 7/1980 |
| DE | 4339713 A1 | 5/1995 |

(Continued)

OTHER PUBLICATIONS

Translation of the International Preliminary Report on Patentability for PCT/EP2010/069637 dated Sep. 10, 2012.

(Continued)

*Primary Examiner* — Cam N. Nguyen
(74) *Attorney, Agent, or Firm* — Drinker Biddle & Reath LLP

(57) ABSTRACT

The present invention relates to an eggshell catalyst comprising an active metal selected from the group consisting of ruthenium, rhodium, palladium, platinum and mixtures thereof, applied to a support material comprising silicon dioxide, wherein the pore volume of the support material is 0.6 to 1.0 ml/g, determined by Hg porosimetry, the BET surface area is 280 to 500 $m^2/g$, and at least 90% of the pores present have a diameter of 6 to 12 nm, to a process for preparing this eggshell catalyst, to a process for hydrogenating an organic compound which comprises at least one hydrogenatable group using the eggshell catalyst, and to the use of the eggshell catalyst for hydrogenating an organic compound.

10 Claims, No Drawings

(56) References Cited

U.S. PATENT DOCUMENTS

| | | |
|---|---|---|
| 2004/0176549 A1 | 9/2004 | Bottcher et al. |
| 2004/0176619 A1 | 9/2004 | Vanoppen et al. |
| 2006/0041167 A1 | 2/2006 | Grass et al. |
| 2006/0183936 A1 | 8/2006 | Grass et al. |
| 2007/0149793 A1 | 6/2007 | Arndt et al. |
| 2008/0200703 A1 | 8/2008 | Van Laar et al. |
| 2009/0305869 A1 | 12/2009 | Henkelmann et al. |
| 2010/0152436 A1 | 6/2010 | Laar et al. |
| 2011/0065572 A1* | 3/2011 | Olken et al. ............ 502/241 |
| 2011/0144398 A1 | 6/2011 | Mirk et al. |

FOREIGN PATENT DOCUMENTS

| | | | |
|---|---|---|---|
| DE | 19634880 A1 | 10/1997 | |
| DE | 19624835 A1 | 1/1998 | |
| DE | 19734974 A1 | 2/1999 | |
| DE | 101 28 205 A1 | 12/2002 | |
| DE | 102005029200 | 12/2006 | |
| DE | 102005029294 * | 1/2007 | B01J 21/08 |
| DE | 102005029294 A1 | 1/2007 | |
| EP | 0243894 A2 | 11/1987 | |
| EP | 0 814 098 A2 | 12/1997 | |
| EP | 1042273 A1 | 10/2000 | |
| EP | 1169285 A1 | 1/2002 | |
| EP | 1266882 A1 | 12/2002 | |
| GB | 1452087 A | 10/1976 | |
| JP | 2007-515276 A | 6/2007 | |
| JP | 2008238043 A | 10/2008 | |
| JP | 2008-543551 A | 12/2008 | |
| WO | WO-9304774 A1 | 3/1993 | |
| WO | WO-99/32427 A1 | 7/1999 | |
| WO | WO-0063142 A1 | 10/2000 | |
| WO | WO-02100537 A2 | 12/2002 | |
| WO | WO-02100538 A2 | 12/2002 | |
| WO | WO-03/004585 A1 | 1/2003 | |
| WO | WO-03/103830 A1 | 12/2003 | |
| WO | WO-2004/009526 A1 | 1/2004 | |
| WO | WO-2006/136541 A2 | 12/2006 | |
| WO | WO-2006136451 A1 | 12/2006 | |
| WO | WO-2006136541 A2 | 12/2006 | |
| WO | WO-2008/015135 A2 | 2/2008 | |
| WO | WO-2008015103 A2 | 2/2008 | |
| WO | WO-2008015170 A2 | 2/2008 | |

OTHER PUBLICATIONS

International Search Report of PCT/EP2010/068911, mailed Aug. 19, 2011.

International Search Report for PCT/EP2010/069637 mailed Feb. 22, 2012.

* cited by examiner

US 9,084,983 B2

CATALYST AND PROCESS FOR HYDROGENATING AROMATICS

CROSS-REFERENCE TO RELATED APPLICATIONS

This application is a national stage application (under 35 U.S.C. §371) of PCT/EP2010/069637, filed Dec. 14, 2010, which claims benefit of European Application No. 09179201.0, filed Dec. 15, 2009, all if which are incorporated herein by reference.

The present invention relates to an eggshell catalyst comprising an active metal selected from the group consisting of ruthenium, rhodium, palladium, platinum and mixtures thereof, applied to a support material comprising silicon dioxide, wherein the pore volume of the support material is 0.6 to 1.0 ml/g, determined by Hg porosimetry, the BET surface area is 280 to 500 $m^2/g$, and at least 90% of the pores present have a diameter of 6 to 12 nm, to a process for preparing this eggshell catalyst, to a process for hydrogenating an organic compound which comprises at least one hydrogenatable group using the eggshell catalyst, and to the use of the eggshell catalyst for hydrogenating an organic compound.

The literature discloses various hydrogenation processes. Of industrial interest are especially the hydrogenation of substituted and unsubstituted aromatic compounds, benzenepolycarboxylic acids, phenol derivatives or aniline derivatives. Additionally of interest are also the hydrogenation products of compounds with C—C, C—O, N—O and C—N multiple bonds and polymers. The processes described in the prior art for hydrogenation of organic compounds are performed in the presence of appropriate catalysts, especially supported catalysts, i.e. an active metal is applied to a support material.

WO 2006/136541 A2 discloses a catalyst and a process for hydrogenating organic compounds comprising hydrogenatable groups. The process according to this document uses an eggshell catalyst which comprises, as the active metal, ruthenium alone or together with at least one further metal of transition groups IB, VIIB or VIII of the Periodic Table of the Elements, applied to a support comprising silicon dioxide as the support material. Additionally disclosed are a process for preparing this eggshell catalyst, a process for hydrogenating an organic compound which comprises hydrogenatable groups, and the use of the corresponding catalyst in the hydrogenation of organic compounds which comprise a hydrogenatable group. The eggshell catalyst used in this process is notable in that the active metal is present in a particularly high proportion in a penetration depth of 300 to 1000 μm, relative to the support material surface.

DE 197 34 974 A1 discloses a process for preparing metal nanoparticle-containing catalysts with porous supports, especially for the gas phase oxidation of ethylene and acetic acid to vinyl acetate. The catalyst according to this document may be an eggshell catalyst, where the surface area of the support material lis, measured by the BET method, is generally from 10 to 500 $m^2/g$; the pore volume is generally 0.3 to 1.2 ml/g. Suitable active metals include rhodium, ruthenium, palladium or platinum. The support material according to this document is nanoporous, with nanopores having a pore size in the range from 1 to 500 nm being present.

WO 99/32427 discloses a process for hydrogenating benzenepolycarboxylic acids or derivatives thereof using a macropore-comprising catalyst. This catalyst comprises, as the active metal, ruthenium alone or together with at least one metal of transition group I, VII or VIII of the Periodic Table, applied to a support which has macropores. More particularly, the pores of the support material have a mean diameter of at least 50 nm and a BET surface area of at most 30 $m^2/g$.

EP 0 814 098 B1 discloses a process for converting an organic compound in the presence of a supported ruthenium catalyst. The catalyst according to this document comprises, as the active metal, ruthenium alone or together with at least one metal of transition group I, VII or VIII of the Periodic Table in an amount of 0.01 to 30% by weight, based on the total weight of the catalyst, applied to a support, where 10 to 50% of the pore volume of the support is formed by macropores with a diameter in the range from 50 nm to 10 000 nm.

EP 1 266 882 B1 discloses a process for preparing cyclohexanedicarboxylic esters by hydrogenating the corresponding benzenedicarboxylic esters in the presence of a suitable catalyst. The catalyst according to this document comprises, as the active metal, nickel in an amount of 5 to about 70% by weight.

WO 2004/009526 A1 likewise discloses a microporous catalyst and a process for hydrogenating aromatic compounds using this catalyst. The document cited mentions catalysts which have a mean pore diameter of 5 to 20 nm and a BET surface area of >50 $m^2/g$. The amount of active ruthenium metal is 0.1 to 30% by weight, and the BET surface area is between 1 and 350 $m^2/g$. The pore volume of the support material used, for example silicon dioxide, is at low values of 0.28 to 0.43 ml/g.

WO 03/103830 A1 discloses a catalyst and a process for hydrogenating aromatic compounds using this catalyst. The catalyst according to this document comprises, as the active material, at least one metal of transition group VIII and a support material with a mean pore diameter of 25 to 50 nm and a specific surface area of >30 $m^2/g$.

DE 196 24 835 A1 discloses a process for hydrogenating polymers with ruthenium or palladium catalysts. The support material of the catalyst according to this document has a specific pore size distribution where 10 to 50% of the pore volume of the support is formed by macropores with a pore diameter in the range from 50 nm to 10 000 nm, and 50 to 90% of the pore volume of the support by mesopores having a pore diameter in the range from 2 to 50 nm. In addition, the catalyst according to this document is an unsupported catalyst, which means that the active metal is present distributed over the entire cross section of the catalyst particles.

The catalysts which are known from the prior art, and the processes for hydrogenating aromatic compounds using these catalysts, are still in need of improvement. Firstly, the conversion of desired target compound, for example of a carbocyclic aliphatic compound, derived from the corresponding aromatic compound, should be increased. In addition, the selectivity of the catalysts with regard to the desired product can still be increased.

It is thus an object of the present invention with respect to the prior art to provide a catalyst which, in the hydrogenation of organic compounds, gives a maximum conversion with simultaneously particularly high selectivity for the desired target product. In addition, the inventive catalysts should be notable for a particularly high stability, i.e. a particularly long lifetime.

These objects are achieved in accordance with the invention by an eggshell catalyst comprising an active metal selected from the group consisting of ruthenium, rhodium, palladium, platinum and mixtures thereof, applied to a support material comprising silicon dioxide, wherein the pore volume of the support material is 0.6 to 1.0 ml/g, determined by Hg porosimetry, the BET surface area is 280 to 500 m²/g, and at least 90% of the pores present have a diameter of 6 to 12 nm.

Further ways of achieving the objects mentioned in accordance with the invention are a process for preparing this catalyst, and a process for hydrogenating organic compounds which have at least one hydrogenatable group.

The achievement of the object mentioned is based on an eggshell catalyst comprising an active metal selected from the group consisting of ruthenium, rhodium, palladium, platinum and mixtures thereof, which has a very specific combination of particular features which impart a particularly high activity and selectivity to the catalyst, for example in the hydrogenation of organic compounds.

The inventive eggshell catalyst comprises an active metal selected from the group consisting of ruthenium, rhodium, palladium, platinum and mixtures thereof, preferably ruthenium, most preferably ruthenium as the sole active metal.

In the inventive eggshell catalyst, the amount of the active metal is generally <1% by weight, preferably 0.1 to 0.5% by weight, more preferably 0.25 to 0.35% by weight, based on the total weight of the catalyst.

The present invention therefore preferably relates to the inventive eggshell catalyst wherein the amount of the active metal is 0.1 to 0.5% by weight, more preferably 0.25 to 0.35% by weight, based on the total weight of the catalyst.

Eggshell catalysts are known per se to those skilled in the art. In the context of the present invention, the term "eggshell catalyst" means that the at least one active metal present, preferably ruthenium, is present predominantly in an outer shell of the support material.

In the inventive eggshell catalysts, preferably 40 to 70% by weight, more preferably 50 to 60% by weight, of the active metal, based on the total amount of the active metal, is present in the shell of the catalyst down to a penetration depth of 200 μm. In a particularly preferred embodiment, 60 to 90% by weight, most preferably 70 to 80% by weight, of the active metal, based on the total amount of the active metal, is present in the shell of the catalyst down to a penetration depth of 500 μm. The aforementioned data are determined by means of SEM (scanning electron microscopy) ERMA (electron probe microanalysis)—EDXS (energy dispersive X-ray spectroscopy) and constitute averaged values. Further information regarding the aforementioned analysis methods and techniques are disclosed, for example, in "Spectroscopy in Catalysis" by J. W. Niemantsverdriet, VCH, 1995 or "Handbook of Microscopy" by S. Amelinckx et al.

To determine the penetration depth of the active metal particles, several catalyst particles (e.g. 3, 4 or 6) are abraded slightly. By means of line scans, the profiles of the active metal/Si concentration ratios are then detected. On each measurement line, several, for example 15 to 20, measurement points are measured at equal intervals; the measurement spot size is approximately 10 μm*10 μm. After integration of the amount of active metal over the depth, the frequency of the active metal in a zone can be determined.

The inventive eggshell catalyst is preferably notable in that the predominant amount of the active metal is present in the shell down to a penetration depth of preferably 200 μm, i.e. close to the surface of the eggshell catalyst. In contrast, in the interior (core) of the catalyst, preferably only a very small amount, if any, of the active metal is present. It has been found that, surprisingly, the inventive catalyst—in spite of the small amount of active metal—owing to the specific combination of particular features has a very high activity in the hydrogenation of organic compounds which comprise at least one hydrogenatable group, especially in the hydrogenation of carbocyclic aromatic groups, coupled with very good selectivities. More particularly, the activity of the inventive catalyst does not decrease over a long hydrogenation period.

Very particular preference is given to an inventive eggshell catalyst in which no active metal can be detected in the interior of the catalyst, i.e. active metal is present only in the outermost shell, for example in a zone down to a penetration depth up to 500 μm.

Most preferably, the amount of the active metal, based on the concentration ratio of active metal to Si, at the surface of the eggshell catalyst is 2 to 25%, preferably 4 to 10%, more preferably 4 to 6%, determined by means of SEM ERMA—EDXS. The surface is analyzed by means of area analyses of areas of 800 μm×2000 μm and with an information depth of approximately 2 μm. The element composition is determined in % by weight (normalized to 100% by weight). The mean concentration ratio (active metal/Si) is averaged over 10 measurement areas.

The surface of the eggshell catalyst is understood in the context of the present application to mean the outer shell of the catalyst down to a penetration depth of approximately 2 μm. This penetration depth corresponds to the information depth in the aforementioned surface analysis.

Very particular preference is given to an eggshell catalyst in which the amount of the active metal, based on the weight ratio of active metal to Si (wt./wt. in %), at the surface of the eggshell catalyst is 4 to 6% by weight, at a penetration depth of 50 μm is 1.5 to 3% by weight, and in the range of penetration depth 50 to 150 μm is 0.5 to 2% by weight, determined by means of SEM EPMA (EDXS). The values mentioned constitute averaged values.

In addition, the size of the active metal particles preferably decreases with increasing penetration depth, determined by means of (FEG)-TEM analysis.

The active metal is preferably present partly or fully in crystalline form in the inventive eggshell catalyst. In preferred cases, ultrafine crystalline active metal can be detected in the shell of the inventive eggshell catalyst by means of SAD (Selected Area Diffraction).

The inventive eggshell catalyst may additionally comprise alkaline earth metal ions ($M^{2+}$), i.e. M=Be, Mg, Ca, Sr and/or Ba, especially Mg and/or Ca, very particularly Mg. The content of alkaline earth metal ion/s ($M^{2+}$) in the catalyst is preferably 0.01 to 1% by weight, especially 0.05 to 0.5% by weight, very particularly 0.1 to 0.25% by weight, based in each case on the weight of the silicon dioxide support material.

A significant constituent of the inventive catalysts is the support material comprising silicon dioxide, preferably amorphous silicon dioxide. The term "amorphous" is understood in this context such that the proportion of crystalline silicon dioxide phases makes up less than 10% by weight of the support material. The support materials used to prepare the catalysts may, however, have superstructures which are formed by regular arrangement of pores in the support material.

Useful support materials are in principle amorphous silicon dioxide types which consist of silicon dioxide at least to an extent of 90% by weight, where the remaining 10% by weight, preferably not more than 5% by weight, of the support material may also be another oxidic material, for example MgO, CaO, $TiO_2$, $ZrO_2$ and/or $Al_2O_3$.

In a preferred embodiment of the invention, the support material is halogen-free, especially chlorine-free, i.e. the halogen content in the support material is generally less than 500 ppm by weight, for example in the range from 0 to 400 ppm by weight. Preference is therefore given to an eggshell catalyst which comprises less than 0.05% by weight of halide (determined by ion chromatography), based on the total weight of the catalyst. The halide content of the support material is more preferably below the analytical detection limit.

Preference is given to support materials comprising silicon dioxide which have a specific surface area in the range from 280 to 500 m$^2$/g, more preferably 280 to 400 m$^2$/g, most preferably 300 to 350 m$^2$/g (BET surface area to DIN 66131).

They may either be of natural origin or may have been produced synthetically. Examples of suitable amorphous support materials based on silicon dioxide are silica gels, kieselguhr, fumed silicas and precipitated silicas. In a preferred embodiment of the invention, the catalysts comprise silica gels as support materials.

According to the invention, the pore volume of the support material is 0.6 to 1.0 ml/g, preferably 0.65 to 0.9 ml/g, for example 0.7 to 0.8 ml/g, determined by Hg porosimetry (DIN 66133).

In the inventive eggshell catalyst, at least 90% of the pores present have a pore diameter of 6 to 12 nm, preferably 7 to 11 nm, more preferably 8 to 10 nm. The pore diameter can be determined by processes known to those skilled in the art, for example by Hg porosimetry or N$_2$ physisorption. In a preferred embodiment, at least 95%, more preferably at least 98%, of the pores present have a pore diameter of 6 to 12 nm, preferably 7 to 11 nm, more preferably 8 to 10 nm.

In the inventive eggshell catalyst, in a preferred embodiment, no pores smaller than 5 nm are present. In addition, in the inventive eggshell catalyst, there are no pores larger than 25 nm, especially larger than 15 nm. In this context, "no pores" means that no pores with these diameters are found by customary analysis methods, for example Hg porosimetry or N$_2$ physisorption.

In the inventive eggshell catalyst, within the measurement precision of the analysis used, there are no macropores, but exclusively mesopores.

In the case of the preferred use of the inventive eggshell catalyst in fixed catalyst beds, it is customary to use shaped bodies of the support material which are obtainable, for example, by extrusion or tableting, and which may have, for example, the form of spheres, tablets, cylinders, extrudates, rings or hollow cylinders, stars and the like, more preferably spheres. The dimensions of these shaped bodies vary typically within the range from 0.5 mm to 25 mm. Preference is given to using catalyst spheres with sphere diameters of 1.0 to 6.0 mm, more preferably 2.5 to 5.5 mm.

In the inventive eggshell catalyst, the dispersity of the active metal is preferably 30 to 60%, more preferably 30 to 50%. Processes for measuring the dispersity of the active metal are known per se to those skilled in the art, for example by pulse chemisorption, wherein the determination of the noble metal dispersion (specific metal surface area, crystal size) is carried out by the CO pulse method (DIN 66136(1-3)).

The present invention therefore preferably relates to an inventive eggshell catalyst in which the dispersity of the active metal is 30 to 60%, more preferably 30 to 50%.

In the inventive eggshell catalyst, the surface area of the active metal is preferably 0.2 to 0.8 m$^2$/g, more preferably 0.3 to 0.7 m$^2$/g. Processes for measuring the surface area of the active metal are known per se to those skilled in the art.

The present invention therefore preferably relates to an inventive eggshell catalyst wherein the surface area of the active metal is 0.2 to 0.8 m$^2$/g, more preferably 0.3 to 0.7 m$^2$/g.

The inventive eggshell catalyst preferably has a tapped density of 400 to 600 g/l, more preferably 450 to 550 g/l.

The present invention therefore preferably relates to an inventive eggshell catalyst which has a tapped density of 400 to 600 g/l, more preferably 450 to 550 g/l.

When the inventive eggshell catalyst is used in the hydrogenation of organic compounds, the very specific combination of features of the silicon dioxide-comprising support material with a specific pore volume, a specific BET surface area and a very specific pore diameter imparts a particularly high activity and selectivity for the desired products thereto.

The present invention therefore preferably relates to an inventive eggshell catalyst comprising ruthenium as the active metal applied to a support material comprising silicon dioxide, where the pore volume of the support material is 0.6 to 1.0 ml/g, preferably 0.65 to 0.9 ml/g, for example 0.7 to 0.8 ml/g, determined by Hg porosimetry (DIN 66133) and N$_2$ adsorption (DIN 66131), the BET surface area is 280 to 500 m$^2$/g, preferably 280 to 400 m$^2$/g, more preferably 300 to 350 m$^2$/g (BET surface area to DIN 66131), and at least 90%, preferably at least 95%, more preferably at least 98%, of the pores present have a diameter of 6 to 12 nm, preferably 7 to 11 nm, more preferably 8 to 10 nm.

The inventive eggshell catalysts are preferably prepared by first impregnating the support material with a solution comprising a precursor compound of the active metal once or more than once, drying the resulting solid and then reducing it. The individual process steps are described in detail below.

The present application therefore further provides a process for preparing an eggshell catalyst according to any of claims 1 to 5, comprising the steps of:
(A) impregnating the support material comprising silicon dioxide once or more than once with a solution comprising at least one precursor compound of the active metal,
(B) then drying,
(C) then reducing.

Step (A)

In step (A), the support material comprising silicon dioxide is impregnated once or more than once with a solution comprising at least one precursor compound of the active metal. In general, suitable precursor compounds are all precursor compounds of the active metal which can be converted under the inventive process conditions to metallic active metal, for example nitrates, acetonates and acetates, preference being given to acetates. In the case preferred in accordance with the invention that the active metal is ruthenium, for example, ruthenium (III) acetate is preferred. Further preferred precursor compounds are palladium(II) acetate, platinum (II) acetate and/or rhodium (II) acetate.

Since the amount of active metal in the inventive eggshell catalyst is very small, in a preferred embodiment, a simple impregnation is effected.

It has been found that, surprisingly, in the case of use of ruthenium (III) acetate as a precursor compound, it is possible to obtain eggshell catalysts which are notable, among other features, in that the significant portion of the active metal, preferably ruthenium alone, is present in the eggshell catalyst down to a penetration depth of 200 μm. The interior of the eggshell catalyst has only little active metal, if any.

Suitable solvents for providing the solution comprising at least one precursor compound are water or else mixtures of water or solvent with up to 50% by volume of one or more water- or solvent-miscible organic solvents, for example mixtures with $C_1$-$C_4$-alkanols such as methanol, ethanol, n-propanol or isopropanol. Aqueous acetic acid or glacial acetic acid may likewise be used. All mixtures should be selected such that one solution or phase is present. Preferred solvents are acetic acid, water or mixtures thereof. Particular preference is given to using a mixture of water and acetic acid as a solvent, since ruthenium (III) acetate is typically present dissolved in acetic acid or glacial acetic acid. The inventive catalyst may also be prepared without use of water.

In the case that more than one active metal is present on the support material, it is possible to apply a plurality of precursor compounds simultaneously. It is also possible that different precursor compounds are applied successively by repeated impregnation. Each impregnation step is typically followed by drying.

Particular preference is given to impregnating with a solution of ruthenium (III) acetate alone in one impregnation step.

The impregnation of the support material can be effected in different ways and depends in a known manner upon the form of the support material. For example, the support material can be sprayed or rinsed with the solution of the precursor compound or the support material can be suspended in the solution of the precursor compound. For example, the support material can be suspended in an aqueous solution of the active metal precursor compound and, after a certain time, filtered off from the aqueous supernatant. The amount of liquid absorbed and the active metal concentration of the solution can then be used to control the active metal content of the catalyst in a simple manner. The support material can also be impregnated by, for example, treating the support with a defined amount of the solution of the active metal precursor compound which corresponds to the maximum amount of liquid that the support material can absorb. For this purpose, the support material can, for example, be sprayed with the required amount of liquid. Suitable apparatus for this purpose is the apparatus used customarily for mixing liquids with solids (see Vauck/Müller, Grundoperationen chemischer Verfahrenstechnik [Basic Operations in Chemical Process Technology], 10th edition, Deutscher Verlag Mr Grundstoffindustrie, 1994, p. 405 ff.), for example tumble driers, impregnating drums, drum mixers, paddle mixers and the like.

Monolithic supports are typically rinsed with the aqueous solutions of the active metal precursor compound.

The solutions used for impregnation are preferably low in halogen, especially low in chlorine, i.e. they comprise zero or less than 500 ppm by weight, especially less than 100 ppm by weight, of halogen, for example from 0 to <80 ppm by weight of halogen based on the total weight of the solution.

The concentration of the active metal precursor compound in the solutions depends, by its nature, upon the amount of active metal precursor compound to be applied and the absorption capacity of the support material for the solution and is <20% by weight, preferably from 0.01 to 6% by weight, more preferably from 0.1 to 1.1% by weight, based on the total mass of the solution used.

Step (B):

The drying can be effected by customary processes for drying solids while maintaining the upper temperature limits specified below. The maintenance of the upper limit of the drying temperatures is important for the quality, i.e. the activity, of the catalyst. Exceedance of the drying temperatures specified below leads to a distinct loss of activity. Calcination of the support at higher temperatures, for example above 300° C. or even 400° C., as the prior art proposes, is not only superfluous but also has a disadvantageous effect on the activity of the catalyst. To achieve sufficient drying rates, the drying is effected preferably at elevated temperature, preferably at ≤180° C., particularly at ≤160° C., and at least 40° C., in particular at least 70° C., especially at least 100° C., very particularly in the range from 110° C. to 150° C.

The solid impregnated with the active metal precursor compound is dried typically under standard pressure, though the drying can also be promoted by employing reduced pressure. Frequently, the drying will be promoted by passing a gas stream over or through the material to be dried, for example air or nitrogen.

The drying time depends, by its nature, upon the desired degree of drying and the drying temperature and is preferably in the range from 1 h to 30 h, preferably in the range from 2 to 10 h.

The drying of the treated support material is preferably conducted to such an extent that the content of water or of volatile solvent constituents before the subsequent reduction makes up less than 5% by weight, in particular not more than 2% by weight, based on the total weight of the solid. The proportions by weight specified relate to the weight loss of the solid, determined at a temperature of 160° C., a pressure of 1 bar and a time of 10 min. In this way, the activity of the catalysts used in accordance with the invention can be enhanced further.

Step (C):

The solid obtained after the drying is converted to its catalytically active form by reducing the solid at temperatures in the range of generally from 150° C. to 450° C., preferably from 250° C. to 350° C., in a manner known per se.

For this purpose, the support material is contacted with hydrogen or a mixture of hydrogen and an inert gas at the above-specified temperatures. The absolute hydrogen pressure is of minor importance for the result of the reduction and can, for example, be varied within the range from 0.2 bar to 1.5 bar. Frequently, the catalyst material is hydrogenated at standard hydrogen pressure in a hydrogen stream. Preference is given to effecting the reduction with movement of the solid, for example by reducing the solid in a rotary tube oven or a rotary sphere oven. In this way, the activity of the inventive catalysts can be enhanced further. The hydrogen used is preferably free of catalyst poisons such as compounds comprising CO and S, for example $H_2S$, COS and others.

The reduction can also be effected by means of organic reducing reagents such as hydrazine, formaldehyde, formates or acetates.

After the reduction, the catalyst can be passivated in a known manner to improve the handling, for example by treating the catalyst briefly with an oxygen-containing gas, for example air, but preferably with an inert gas mixture comprising from 1 to 10% by volume of oxygen. It is also possible here to use $CO_2$ or $CO_2/O_2$ mixtures.

The active catalyst may also be stored under an inert organic solvent, for example ethylene glycol.

To prepare the inventive eggshell catalyst, in a further embodiment, the active metal catalyst precursor, for example prepared as above or prepared as described in WO-A2-02/100538 (BASF AG), can be impregnated with a solution of one or more alkaline earth metal (II) salts.

Suitable alkaline earth metal (II) salts are corresponding nitrates, especially magnesium nitrate and calcium nitrate.

A suitable solvent for the alkaline earth metal (II) salts in this impregnation step is water. The concentration of the alkaline earth metal (II) salt in the solvent is, for example, from 0.01 to 1 mol/liter.

As a result of the preparation, the active metal is present in the inventive catalysts in the form of metallic active metal.

As a result of the use of halogen-free, especially chlorine-free, active metal precursor compounds and solvents in the preparation of the inventive eggshell catalyst, the halide content, especially chloride content, of the inventive eggshell catalysts is additionally below 0.05% by weight (from 0 to <500 ppm by weight, for example in the range of 0-400 ppm by weight), based on the total weight of the catalyst. The chloride content is determined by ion chromatography, for example with the method described below.

In this document, all ppm data are understood to mean parts by weight (ppm by weight), unless stated otherwise.

The support material preferably does not comprise more than 1% by weight and in particular not more than 0.5% by weight and in particular not more than 0.2% by weight of aluminum oxide, calculated as $Al_2O_3$.

Since the condensation of silica can also be influenced by aluminum and iron, the total concentration of Al (III) and Fe(II and/or III) is preferably less than 300 ppm, more preferably less than 200 ppm, and is, for example, in the range from 0 to 180 ppm.

The proportion of alkali metal oxide results preferably from the preparation of the support material and can be up to 2% by weight. Preferably, it is less than 1% by weight. Also suitable are alkali metal oxide-free supports (0 to <0.1% by weight). The proportion of MgO, CaO, $TiO_2$ or of $ZrO_2$ may make up up to 10% by weight of the support material and is preferably not more than 5% by weight. However, suitable support materials are also those which do not comprise any detectable amounts of these metal oxides (from 0 to <0.1% by weight).

Because Al (III) and Fe(II and/or III) can give rise to acidic sites incorporated into silica, it is preferred that charge compensation is present in the carrier, preferably with alkaline earth metal cations ($M^{2+}$, M=Be, Mg, Ca, Sr, Ba). This means that the weight ratio of M (II) to (Al (III)+Fe(II and/or III)) is greater than 0.5, preferably >1, more preferably greater than 3. The Roman numerals in brackets after the element symbol mean the oxidation state of the element.

The inventive eggshell catalyst is preferably used as a hydrogenation catalyst. It is especially suitable for hydrogenating organic compounds which comprise at least one hydrogenatable group.

The hydrogenatable groups may be groups which have the following structural units: C—C double bonds, C—C triple bonds, aromatic groups, C—N double bonds, C—N triple bonds, C—O double bonds, N—O double bonds, C—S double bonds, $NO_2$ groups, where the groups may also be present in polymers or cyclic structures, for example in unsaturated heterocycles. The hydrogenatable groups may each occur once or more than once in the organic compounds. It is also possible that the organic compounds have two or more different groups of the hydrogenatable groups mentioned. Depending on the hydrogenation conditions, it is possible in the latter case that only one or more of the hydrogenatable groups are hydrogenated.

Preference is given to using the inventive eggshell catalysts for hydrogenating a carbocylic aromatic group to the corresponding carbocyclic aliphatic group or for hydrogenating aldehydes to the corresponding alcohols, most preferably for hydrogenating a carbocyclic aromatic group to the corresponding carbocyclic aliphatic group. Particular preference is given to fully hydrogenating the aromatic group, full hydrogenation being understood to mean conversion of the compound to be hydrogenated of generally >98%, preferably >99%, more preferably >99.5%, even more preferably >99.9%, in particular >99.99% and especially >99.995%.

In the case of use of the inventive eggshell catalyst for hydrogenating benzene to cyclohexane, the typical cyclohexane specifications which require a residual benzene content of <100 ppm (which corresponds to a benzene conversion of >99.99%) are fulfilled. The benzene conversion in a hydrogenation of benzene with the inventive eggshell catalyst is preferably >99.995%.

In the case of use of the inventive eggshell catalyst for hydrogenating aromatic dicarboxylic esters, especially phthalic esters to the corresponding dialkyl cyclohexanedicarboxylates, the typical specifications which require a residual content of the aromatic dicarboxylic ester, especially residual phthalic ester content, of <100 ppm (which corresponds to a conversion of >99.99%) are thus likewise fulfilled. The conversion in a hydrogenation of aromatic dicarboxylic esters, especially phthalic esters, with the inventive eggshell catalyst is preferably >99.995%.

The present application therefore further provides a process for hydrogenating an organic compound which comprises at least one hydrogenatable group, preferably for hydrogenating a carbocyclic aromatic group to the corresponding carbocyclic aliphatic group or for hydrogenating aldehydes to the corresponding alcohols, most preferably for hydrogenating a carbocyclic aromatic group to the corresponding carbocyclic aliphatic group, wherein the organic compound is contacted with at least one reducing agent and an inventive eggshell catalyst.

The present invention also relates to the use of the inventive eggshell catalyst in a process for hydrogenating an organic compound which comprises at least one hydrogenatable group. The present invention preferably relates to this inventive use wherein a carbocyclic aromatic group is hydrogenated to the corresponding carbocyclic aliphatic group, or aldehydes to the corresponding alcohols.

The carbocyclic aromatic group is preferably part of an aromatic hydrocarbon which has the following general formula:

$$(A)\text{-}(B)_n$$

in which the symbols are each defined as follows:
A is independently aryl or heteroaryl; A is preferably selected from phenyl, diphenyl, benzyl, dibenzyl, naphthyl, anthracene, pyridyl and quinoline; A is more preferably phenyl;
n is from 0 to 5, preferably from 0 to 4, more preferably from 0 to 3, especially in the case when A is a 6-membered aryl or heteroaryl ring; in the case that A is a 5-membered aryl or heteroaryl ring, n is preferably from 0 to 4; irrespective of the ring size, n is more preferably from 0 to 3, even more preferably from 0 to 2 and in particular from 0 to 1; the remaining hydrocarbon atoms or heteroatoms of A which do not bear any substituents B bear hydrogen atoms or, if appropriate, no substituents;
B is independently selected from the group consisting of alkyl, alkenyl, alkynyl, substituted alkyl, substituted alkenyl, substituted alkynyl, heteroalkyl, substituted heteroalkyl, heteroalkenyl, substituted heteroalkenyl, heteroalkynyl, substituted heteroalkynyl, cycloalkyl, cycloalkenyl, substituted cycloalkyl, substituted cycloalkenyl, COOR where R is H, alkyl, substituted alkyl, cycloalkyl, substituted cycloalkyl, aryl or substituted aryl, halogen, hydroxyl, alkoxy, aryloxy, carbonyl, amino, amido, thio and phosphino; B is preferably selected independently from $C_{1-6}$ alkyl, $C_{1-6}$-alkenyl, $C_{1-6}$-alkynyl, $C_m$-cycloalkyl, $C_{3-8}$-cycloalkenyl, COOR where R is H or $C_{1-12}$-alkyl, hydroxyl, alkoxy, aryloxy, amino and amido; B is more preferably independently $C_{1-6}$-alkyl, COOR where R is H or $C_{1-12}$-alkyl, amino, hydroxyl or alkoxy.

The expression "independently" means that when n is 2 or greater, the substituents B may be identical or different radicals from the groups mentioned.

According to the present application, unless stated otherwise, alkyl is understood to mean branched or linear, saturated acyclic hydrocarbon radicals. Examples of suitable alkyl radicals are methyl, ethyl, n-propyl, i-propyl, n-butyl, t-butyl, i-butyl etc. Preference is given to alkyl radicals having 1 to 50 carbon atoms, more preferably having 1 to 20 carbon atoms, most preferably having from 1 to 6 carbon atoms and in particular having 1 to 3 carbon atoms.

In the abovementioned COOR group, R is H or branched or linear alkyl, preferably H or $C_{1-12}$-alkyl. Preferred alkyl groups are $C_{4-10}$-alkyl groups, more preferably $C_{8-10}$-alkyl groups. These may be branched or unbranched and are preferably branched. The alkyl groups having more than three carbon atoms may be isomer mixtures of different alkyl groups having the same carbon number. One example is a $C_9$-alkyl group which may be an isononyl group, i.e. an isomer mixture of different $C_9$-alkyl groups. The same also applies, for example, to a $C_8$-alkyl group. Such isomer mixtures are obtained starting from the alcohols corresponding to the alkyl groups, which are obtained as isomer mixtures owing to the process for preparing them—which is known to those skilled in the art.

According to the present application, alkenyl is understood to mean branched or unbranched acyclic hydrocarbon radicals which have at least one carbon-carbon double bond. Suitable alkenyl radicals are, for example, 2-propenyl, vinyl, etc. The alkenyl radicals have preferably 2 to 50 carbon atoms, more preferably 2 to 20 carbon atoms, most preferably 2 to 6 carbon atoms and in particular 2 to 3 carbon atoms. The term alkenyl is also understood to mean those radicals which have either a cis orientation or a trans orientation (alternatively E or Z orientation).

According to the present application, alkynyl is understood to mean branched or unbranched acyclic hydrocarbon radicals which have at least one carbon-carbon triple bond. The alkynyl radicals have preferably 2 to 50 carbon atoms, more preferably 2 to 20 carbon atoms, even more preferably 1 to 6 carbon atoms and in particular 2 to 3 carbon atoms.

Substituted alkyl, substituted alkenyl and substituted alkynyl are understood to mean alkyl, alkenyl and alkynyl radicals in which one or more hydrogen atoms which are bonded to a carbon atom of these radicals are replaced by another group. Examples of such other groups are heteroatoms, halogen, aryl, substituted aryl, cycloalkyl, cycloalkenyl, substituted cycloalkyl, substituted cycloalkenyl and combinations thereof. Examples of suitable substituted alkyl radicals are benzyl, trifluoromethyl, among others.

The terms heteroalkyl, heteroalkenyl and heteroalkynyl are understood to mean alkyl, alkenyl and alkynyl radicals in which one or more of the carbon atoms in the carbon chain are replaced by a heteroatom selected from N, O and S.

The bond between the heteroatom and a further carbon atom may be saturated or optionally unsaturated.

According to the present application, cycloalkyl is understood to mean saturated cyclic nonaromatic hydrocarbon radicals which are composed of a single ring or a plurality of fused rings. Suitable cycloalkyl radicals are, for example, cyclopentyl, cyclohexyl, cyclooctanyl, bicyclooctyl, etc. The cycloalkyl radicals have preferably between 3 and 50 carbon atoms, more preferably between 3 and 20 carbon atoms, even more preferably between 3 and 8 carbon atoms and in particular between 3 and 6 carbon atoms.

According to the present application, cycloalkenyl is understood to mean partly unsaturated, cyclic nonaromatic hydrocarbon radicals which have a single ring or a plurality of fused rings. Suitable cycloalkenyl radicals are, for example, cyclopentenyl, cyclohexenyl, cyclooctenyl, etc. The cycloalkenyl radicals have preferably 3 to 50 carbon atoms, more preferably 3 to 20 carbon atoms, even more preferably 3 to 8 carbon atoms and in particular 3 to 6 carbon atoms.

Substituted cycloalkyl and substituted cycloalkenyl radicals are cycloalkyl and cycloalkenyl radicals in which one or more hydrogen atoms of any carbon atom of the carbon ring may be replaced by another group. Such other groups are, for example, halogen, alkyl, alkenyl, alkynyl, substituted alkyl, substituted alkenyl, substituted alkynyl, aryl, substituted aryl, cycloalkyl, cycloalkenyl, substituted cycloalkyl, substituted cycloalkenyl, an aliphatic heterocyclic radical, a substituted aliphatic heterocyclic radical, heteroaryl, substituted heteroaryl, alkoxy, aryloxy, boryl, phosphino, amino, silyl, thio, seleno and combinations thereof. Examples of substituted cycloalkyl and cycloalkenyl radicals are 4-dimethylaminocyclohexyl, 4,5-dibromocyclohept-4-enyl, among others.

In the context of the present application, aryl is understood to mean aromatic radicals which have a single aromatic ring or a plurality of aromatic rings which are fused, joined via a covalent bond or joined by a suitable unit, for example a methylene or ethylene unit. Such suitable units may also be carbonyl units, as in benzophenol, or oxygen units as in diphenyl ether, or nitrogen units as in diphenylamine. The aromatic ring or the aromatic rings are, for example, phenyl, naphthyl, diphenyl, diphenyl ether, diphenylamine and benzophenone. The aryl radicals have preferably 6 to 50 carbon atoms, more preferably 6 to 20 carbon atoms, most preferably 6 to 8 carbon atoms.

Substituted aryl radicals are aryl radicals in which one or more hydrogen atoms which are bonded to carbon atoms of the aryl radical are replaced by one or more other groups. Suitable other groups are alkyl, alkenyl, alkynyl, substituted alkyl, substituted alkenyl, substituted alkynyl, cycloalkyl, cycloalkenyl, substituted cycloalkyl, substituted cycloalkenyl, heterocyclo, substituted heterocyclo, halogen, and halogen-substituted alkyl (e.g. $CF_3$), hydroxyl, amino, phosphino, alkoxy, thio, and both saturated and unsaturated cyclic hydrocarbons which may be fused to the aromatic ring or to the aromatic rings or be joined by a bond, or be joined to one another via a suitable group. Suitable groups have already been mentioned above.

Heteroaryl radicals are understood to mean those aryl radicals in which one or more of the carbon atoms of the aromatic ring of the aryl radical has/have been replaced by a heteroatom selected from N, O and S.

Substituted heteroaryl radicals are understood to mean those substituted aryl radicals in which one or more of the carbon atoms of the aromatic ring of the substituted aryl radical has/have been replaced by a heteroatom selected from N, O and S.

According to the present application, heterocyclo is understood to mean a saturated, partly unsaturated or unsaturated cyclic radical in which one or more carbon atoms of the radical have been replaced by a heteroatom, for example N, O or S (the term "heterocyclo" also includes the aforementioned heteroaryl radicals). Examples of heterocyclo radicals are piperazinyl, morpholinyl, tetrahydropyranyl, tetrahydrofuranyl, piperidinyl, pyrrolidinyl, oxazolinyl, pyridyl, pyrazyl, pyridazyl, pyrimidyl.

Substituted heterocyclo radicals are those heterocyclo radicals in which one or more hydrogen atoms which are bonded to one of the ring atoms are replaced by another group. Suitable other groups are halogen, alkyl, substituted alkyl, aryl, substituted aryl, heteroaryl, substituted heteroaryl, alkoxy, aryloxy, boryl, phosphino, amino, silyl, thio, seleno and combinations thereof.

Alkoxy radicals are understood to mean radicals of the general formula —$OZ^1$ in which $Z^1$ is selected from alkyl, substituted alkyl, cycloalkyl, substituted cycloalkyl, heterocycloalkyl, substituted heterocycloalkyl, silyl and combinations thereof. Suitable alkoxy radicals are, for example, methoxy, ethoxy, benzyloxy, t-butoxy, etc.

The term aryloxy is understood to mean those radicals of the general formula —$OZ^1$ in which $Z^1$ is selected from aryl, substituted aryl, heteroaryl, substituted heteroaryl and combinations thereof. Suitable aryloxy radicals are phenoxy, substituted phenoxy, 2-pyridinoxy, 8-quinolinoxy, among others.

In a preferred embodiment, A is phenyl, n is 0 to 3 and B is $C_{1-6}$-alkyl, COOR where R is H or $C_{1-12}$-alkyl, amino, hydroxyl or alkoxy. The inventive hydrogenation process is effected preferably in such a way that the phenyl group is hydrogenated fully to the corresponding cyclohexyl group.

Preferred compounds which are hydrogenated in accordance with the invention to their corresponding cyclohexyl derivatives are specified below.

In a preferred embodiment of the hydrogenation process according to the invention, the aromatic hydrocarbon is selected from the group consisting of benzene and alkyl-substituted benzenes such as toluene, ethylbenzene, xylene (o-, m-, p- or isomer mixture) and mesitylene (1,2,4 or 1,3,5 or isomer mixture). In the process according to the invention, preference is thus given to hydrogenating benzene to cyclohexane and the alkyl-substituted benzenes such as toluene, ethylbenzene, xylene and mesitylene to alkyl-substituted cyclohexanes such as methylcyclohexane, ethylcyclohexane, dimethylcyclohexane and trimethylcyclohexane. It is also possible to hydrogenate any mixtures of the aforementioned aromatic hydrocarbons to mixtures of the corresponding cyclohexanes. For example, it is possible to use any mixtures comprising two or three compounds selected from benzene, toluene and xylene to mixtures comprising two or three compounds selected from cyclohexane, methylcyclohexane and dimethylcyclohexane.

In a further preferred embodiment of the hydrogenation process according to the invention, the aromatic hydrocarbon is selected from the group consisting of phenol, alkyl-substituted phenols such as 4-tert-butylphenol and 4-nonylphenol, bis(p-hydroxyphenyl)methane and bis(p-hydroxyphenyl) dimethylmethane. In the process according to the invention, preference is thus given to hydrogenating phenol to cyclohexanol, the alkyl-substituted phenols such as 4-tert-butylphenol and 4-nonylphenol to alkyl-substituted cyclohexanols such as 4-tert-butylcyclohexanol and 4-nonylcyclohexanol, bis(p-hydroxyphenyl)methane to bis(p-hydroxycyclohexyl)-methane and bis(p-hydroxyphenyl)dimethylmethane to bis(p-hydroxycyclohexyl)-dimethylmethane.

In a further preferred embodiment of the hydrogenation process according to the invention, the aromatic hydrocarbon is selected from the group consisting of aniline, alkyl-substituted aniline, N,N-dialkylaniline, diaminobenzene, bis(p-aminophenyl)methane and bis(p-aminotolyl)methane. In the process according to the invention, preference is thus given to hydrogenating aniline to cyclohexylamine, alkyl-substituted aniline to alkyl-substituted cyclohexylamine, N,N-dialkylaniline to N,N-dialkylcyclohexylamine, diaminobenzene to diaminocyclohexane, bis(p-aminophenyl)methane to bis(p-aminocyclohexyl)methane and bis(p-amino-tolyl)methane to bis(p-aminomethylcyclohexyl)methane.

In a further preferred embodiment of the hydrogenation process according to the invention, the aromatic hydrocarbon is selected from the group consisting of aromatic carboxylic acids such as phthalic acid and aromatic carboxylic esters such as $C_{1-12}$-alkyl esters of phthalic acid, where the $C_{1-12}$-alkyl radicals may be linear or branched, for example dimethyl phthalate, di-2-propylheptyl phthalate, di-2-ethylhexyl phthalate, dioctyl phthalate, diisononyl phthalate. In the process according to the invention, preference is thus given to hydrogenating aromatic carboxylic acids such as phthalic acid to cycloaliphatic carboxylic acids such as tetrahydrophthalic acid and aromatic carboxylic esters such as $C_{1-12}$-alkyl esters of phthalic acid to aliphatic carboxylic esters such as $C_{1-12}$-alkyl esters of tetrahydrophthalic acid, for example dimethyl phthalate to dimethyl cyclohexanedicarboxylate, di-2-propylheptyl phthalate to di-2-propylheptyl cyclohexanedicarboxylate, di-2-ethylhexyl phthalate to di-2-ethylhexyl cyclohexanedicarboxylate, dioctyl phthalate to dioctyl cyclohexanedicarboxylate and diisononyl phthalate to diisononyl cyclohexanedicarboxylate.

In the process according to the invention, the organic compound which has at least one carbocyclic aromatic group is most preferably selected from the group consisting of benzene, alkyl-substituted benzenes, phenol, alkyl-substituted phenols, aniline, alkyl-substituted aniline, N,N-dialkylaniline, diaminobenzene, bis(p-aminophenyl)methane, bis(p-aminotolyl)methane, aromatic carboxylic acids, aromatic carboxylic esters and mixtures thereof.

The organic compound which at least one organic compound which has at least one carbocyclic aromatic group is especially preferably selected from the group consisting of benzene, diisononyl phthalate, benzoic acid, 2-methylphenol, bisphenol A, cuminaldehyde, aniline, methylenedianiline, ortho-toluidine base, xylidine base and mixtures thereof.

In a further embodiment, the present application relates to a process for hydrogenating aldehydes to the corresponding alcohols. Preferred aldehydes are mono- and disaccharides such as glucose, lactose and xylose. The mono- and disaccharides are hydrogenated to the corresponding sugar alcohols, for example glucose is hydrogenated to sorbitol, lactose to lactitol and xylose to xylitol.

Suitable mono- and disaccharides and suitable hydrogenation conditions are disclosed, for example, in DE-A 101 28 205, the eggshell catalyst according to the present invention being used instead of the catalyst disclosed in DE-A 101 28 205.

The hydrogenation process according to the invention is a selective process for hydrogenating organic compounds which comprise hydrogenatable groups, preferably for hydrogenating a carbocyclic aromatic group to the corresponding carbocyclic aliphatic group, with which high yields and space-time yields, [amount of product/(volume of catalyst·time)] (kg/($I_{cat.}$·h)), [amount of product/(reactor volume·time)] (kg/($I_{reactor}$·h)), based on the catalyst used, can be achieved, and in which the catalysts used can be used repeatedly for hydrogenations without workup. In particular, long catalyst service lives are achieved in the hydrogenation process according to the invention.

The hydrogenation process according to the invention may be performed in the liquid phase or in the gas phase. Preference is given to carrying out the hydrogenation process according to the invention in the liquid phase.

The hydrogenation process according to the invention may be performed in the absence of a solvent or diluent or presence of a solvent or diluent, i.e. it is not essential to carry out the hydrogenation in solution.

The solvent or diluent used may be any suitable solvent or diluent. Useful solvents or diluents are in principle those which are capable of dissolving the organic compound to be hydrogenated to a maximum extent or mix completely with it and which are inert under the hydrogenation conditions, i.e. are not hydrogenated.

Examples of suitable solvents are cyclic and acyclic ethers, for example tetrahydrofuran, dioxane, methyl tert-butyl ether, dimethoxyethane, dimethoxypropane, dimethyldiethylene glycol, aliphatic alcohols such as methanol, ethanol, n- or isopropanol, n-, 2-, iso- or tert-butanol, carboxylic esters such as methyl acetate, ethyl acetate, propyl acetate or butyl acetate, and also aliphatic ether alcohols such as methoxypropanol, and cycloaliphatic compounds such as cyclohexane, methylcyclohexane and dimethylcyclohexane.

The amount of the solvent or diluent used is not restricted in any particular way and can be freely selected depending on the requirement, although preference is given to amounts which lead to a 3 to 70% by weight solution of the organic compound intended for hydrogenation. The use of a diluent is advantageous in order to prevent strong exothermicity in the hydrogenation process. Excessive exothermicity can lead to deactivation of the catalyst and is therefore undesired. Careful temperature control is therefore advisable in the hydrogenation process according to the invention. Suitable hydrogenation temperatures are specified below.

When a solvent is used in the process according to the invention, particular preference is given to using the product formed in the hydrogenation, i.e. preferably the particular cycloaliphatic(s), if appropriate in addition to other solvents or diluents. In any case, a portion of the product formed in the process can be added to the aromatic yet to be hydrogenated. In the hydrogenation of benzene, cyclohexane is thus used as a solvent in a particularly preferred embodiment. In the hydrogenation of phthalates, preference is given to using the corresponding dialkylcyclohexanedicarboxylic esters as solvents.

Based on the weight of the organic compound intended for hydrogenation, preference is given to adding 1 to 30 times, more preferably 5 to 20 times, in particular 5 to 10 times the amount of product as the solvent or diluent. In particular, the present invention relates to a hydrogenation of the type in question here, in which benzene is hydrogenated to cyclohexane in the presence of the inventive catalyst.

The actual hydrogenation is effected typically in analogy to the known hydrogenation processes for hydrogenating organic compounds which have hydrogenatable groups, preferably for hydrogenating a carbocyclic aromatic group to the corresponding carbocyclic aliphatic group, as are described in the prior art cited at the outset. To this end, the organic compound as a liquid phase or gas phase, preferably as a liquid phase, is contacted with the catalyst in the presence of hydrogen. The liquid phase can be passed over a fluidized catalyst bed (fluidized bed mode) or a fixed catalyst bed (fixed bed mode).

The present invention therefore preferably relates to the process according to the invention wherein the hydrogenation is effected in a fixed bed reactor.

The hydrogenation may be configured either continuously or batchwise, preference being given to the continuous process performance. Preference is given to carrying out the process according to the invention in trickle reactors or in flooded mode by the fixed bed mode. The hydrogen may be passed over the catalyst either in cocurrent with the solution of the reactant to be hydrogenated or in countercurrent.

Suitable apparatus for performing a hydrogenation by hydrogenation over a fluidized catalyst bed and over a fixed catalyst bed are known from the prior art, for example from Ullmanns Enzyklopadie der Technischen Chemie, 4$^{th}$ edition, volume 13, p. 135 ff., and also from P. N. Rylander, "Hydrogenation and Dehydrogenation" in Ullmann's Encyclopedia of Industrial Chemistry, 5$^{th}$ ed. on CD-ROM.

The inventive hydrogenation may be performed either at standard hydrogen pressure or at elevated hydrogen pressure, for example at an absolute hydrogen pressure of at least 1.1 bar, preferably at least 2 bar. In general, the absolute hydrogen pressure will not exceed a value of 325 bar and preferably 300 bar. More preferably, the absolute hydrogen pressure is in the range from 1.1 to 300 bar, most preferably in the range from 5 to 40 bar. The hydrogenation of benzene is effected, for example, at a hydrogen pressure of generally ≤50 bar, preferably 10 bar to 45 bar, more preferably 15 to 40 bar.

The reaction temperatures in the process according to the invention are generally at least 30° C. and will frequently not exceed a value of 250° C. Preference is given to performing the hydrogenation process at temperatures in the range from 50 to 200° C., more preferably from 70 to 180° C. and most preferably in the range from 80 to 160° C. The hydrogenation of benzene is effected, for example, at temperatures in the range from generally 75° C. to 170° C., preferably 80° C. to 160° C.

Useful reaction gases in addition to hydrogen are also hydrogenous gases which do not comprise any catalyst poisons such as carbon monoxide or sulfur-containing gases such as $H_2S$ or COS, for example mixtures of hydrogen with inert gases such as nitrogen or reformer offgases which typically still comprise volatile hydrocarbons. Preference is given to using pure hydrogen (purity ≥99.9% by volume, particularly ≥99.95% by volume, in particular 99.99% by volume).

Owing to the high catalyst activity, comparatively small amounts of catalyst are required based on the reactant used. For instance, in the batchwise suspension mode, preferably less than 5 mol %, for example 0.2 mol % to 2 mol %, of active metal will be used based on 1 mole of reactant. In continuous configuration of the hydrogenation process, the reactant to be hydrogenated will typically be conducted over the catalyst in an amount of 0.05 to 3 kg/(l(catalyst)·h), in particular 0.15 to 2 kg/(l(catalyst)·h).

It will be appreciated that the catalysts used in this process, in the event of declining activity, can be regenerated by the methods which are customary for noble metal catalysts such as ruthenium catalysts and are known to those skilled in the art. Mention should be made here, for example, of the treatment of the catalyst with oxygen as described in BE 882 279, the treatment with dilute, halogen-free mineral acids as described in U.S. Pat. No. 4,072,628, or the treatment with hydrogen peroxide, for example in the form of aqueous solutions having a content of 0.1 to 35% by weight, or the treatment with other oxidizing substances, preferably in the form of halogen-free solutions. Typically, the catalyst will be rinsed with a solvent, for example water, after being reactivated and before being used again.

The organic compounds which comprise hydrogenatable groups and are used in the hydrogenation process according to the invention (preferred compounds are mentioned above) have, in a preferred embodiment of the process according to the invention, a sulfur content of generally ≤2 mg/kg, preferably ≤1 mg/kg, more preferably ≤0.5 mg/kg, even more preferably ≤0.2 mg/kg and in particular ≤0.1 mg/kg. The method of determining the sulfur content is mentioned below. A sulfur content of ≤0.1 mg/kg means that no sulfur is detected in the feedstock, for example benzene, with the analysis method specified below.

In the case of the preferred hydrogenation of carbocyclic aromatic groups to the corresponding carbocyclic aliphatic groups, the hydrogenation process according to the invention preferably features the full hydrogenation of the aromatic rings of the organic compounds used with carbocyclic aromatic groups, the degree of hydrogenation being generally >98%, preferably >99%, more preferably >99.5%, even more preferably >99.9%, in particular >99.99% and especially >99.995%.

The degree of hydrogenation is determined by gas chromatography. In the case of hydrogenation of dicarboxylic acids and dicarboxylic esters, especially phthalates, the degree of hydrogenation is determined by means of UV/VIS spectrometry.

A particularly preferred embodiment of the hydrogenation process according to the invention relates to the hydrogenation of benzene to cyclohexane. The hydrogenation process according to the invention will therefore be described in detail below using the example of benzene hydrogenation.

The hydrogenation of benzene is effected generally in the liquid phase. It may be performed continuously or batchwise, preference being given to continuous performance.

The benzene hydrogenation according to the invention is effected generally at a temperature of 75° C. to 170° C., preferably 80° C. to 160° C. The pressure is generally ≤50 bar, preferably 10 bar to 45 bar, more preferably 15 bar to 40 bar, most preferably 18 to 38 bar.

The benzene used in the hydrogenation process according to the invention has, in a preferred embodiment of the process according to the invention, a sulfur content of generally ≤2 mg/kg, preferably ≤1 mg/kg, more preferably ≤0.5 mg/kg, even more preferably ≤0.2 mg/kg and in particular ≤0.1 mg/kg. The method of determining the sulfur content is mentioned below. A sulfur content of ≤0.1 mg/kg means that no sulfur can be detected in the benzene with the analysis method specified below.

The hydrogenation can be performed generally in the fluidized bed or fixed bed mode, preference being given to performance in the fixed bed mode. Particular preference is given to performing the hydrogenation process according to the invention with liquid circulation, in which case the heat of hydrogenation can be removed by means of a heat exchanger and utilized. The feed/circulation ratio in the case of performance of the hydrogenation process according to the invention with liquid circulation is generally 1:5 to 1:40, preferably 1:10 to 1:30.

In order to achieve full conversion, postreaction of the hydrogenation discharge may be effected. To this end, the hydrogenation discharge may be passed through a downstream reactor after the hydrogenation process according to the invention in the gas phase or in the liquid phase in straight pass. In the case of liquid phase hydrogenation, the reactor may be operated in trickle mode or operated in flooded mode. The reactor is charged with the inventive catalyst or with another catalyst known to those skilled in the art.

With the aid of the process according to the invention, it is thus possible to obtain hydrogenated products which comprise very small residual contents, if any, of the starting materials to be hydrogenated.

EXAMPLES

Example 1

Catalyst Preparation

Example 1.1

Inventive

AF125 $SiO_2$ supports are used, 3-5 mm spheres, BET 337 m$^2$/g, tapped density 0.49 kg/l, water absorption (WA)=0.83 ml/g, as is ruthenium (III) acetate in acetic acid from Umicore 200 g of supports are initially charged in a round-bottom flask. 14.25% ruthenium acetate solution is weighed into a measuring cylinder and diluted to 150 ml with dist. $H_2O$ (90% WA). The solution is divided into four. The support material is initially charged in a rotary evaporator and the first of the four impregnations is pumped onto the support material at 3-6 rpm with a gentle vacuum. Once the first impregnation is on the support, it is rotated further in the rotary evaporator for 10 min in order to homogenize the catalyst. This step is then repeated three times more until the entire solution is on the support. The impregnated material is dried in motion at 140° C. in a rotary tube furnace, reduced at 200° C. for 3 h (20 l/h of $H_2$; 10 l/h of $N_2$) and passivated (at RT (5% air in $N_2$, 2 h)). The inventive catalyst A thus obtained comprises 0.34% by weight of Ru.

Example 1.2

Comparative Example

Catalyst B is prepared as described in WO 2006/136451 (0.35% Ru/$SiO_2$)

Example 1.3

Comparative Example

Catalyst C is prepared as described in EP 1 042 273 (0.5% Ru/$Al_2O_3$)

Example 2

Hydrogenation Examples

Example 2.1

Hydrogenation of Benzene

A 300 mL pressure reactor is initially charged with 3.4 g of the catalyst A prepared according to Example 1.1 in a catalyst insert basket, which are admixed with 100 g of a 5% solution of benzene in cyclohexane. The hydrogenation is performed with pure hydrogen at a constant pressure of 32 bar and a temperature of 100° C. Hydrogenation is effected for 4 h. The reactor is subsequently decompressed. Conversion is 100%.

Example 2.2

Hydrogenation of Benzene with Catalyst B

A 300 mL pressure reactor is initially charged with 2.5 g of the catalyst B prepared according to Example 1.2 in a catalyst insert basket, which is admixed with 100 g of a 5% solution of benzene in cyclohexane. The hydrogenation is performed with pure hydrogen at a constant pressure of 32 bar and a temperature of 100° C. Hydrogenation is effected for 4 h. The reactor was subsequently decompressed. Conversion was 99.2%.

Example 2.3

Hydrogenation of Diisononyl Phthalate to Diisononyl Cyclohexane-Dicarboxylate (DINCH)

A continuously operated plant consisting of two tubular reactors connected in series (main reactor (MR) 160 mL and postreactor (PR) 100 mL) is charged with the catalyst A prepared according to Example 1.1. (MR: 54.3 g, PR: 33.5 g). The main reactor is operated with circulation in trickle mode, the postreactor in straight pass in liquid phase mode. Palatinol N (diisononyl phthalate; CAS No. 28553-12-0, prepared according to Example 3) (36 g/h; catalyst hourly space velocity=0.3 kg/(L h)) is pumped through the reactor cascade with pure hydrogen at a mean temperature of 122° C. in the main reactor and 122° C. in the postreactor and a constant pressure of 36 bar. The conversion of Palatinol N is 100%; the selectivity based on DINCH is 99.5%. The cis/trans ratio is 94/6-92/8.

Example 2.4

Hydrogenation of Diisononyl Phthalate to Diisononyl Cyclohexane-Dicarboxylate (DINCH) with Catalyst C A continuously operated plant consisting of a tubular reactor (160 mL) is charged with the catalyst C prepared according to Example 1.3 (0.5% Ru on $Al_2O_3$) (78.0 g). The reactor is operated in trickle mode with circulation (liquid hourly space velocity 10 m/h). Palatinol N (diisononyl phthalate; CAS No. 28553-12-0, prepared according to Example 3) (36 g/h; catalyst hourly space velocity=0.3 kg/(L h)) is pumped through the reactor with pure hydrogen at a mean temperature of 132° C., constant pressure of 40 bar. The conversion of Palatinol N is 94.9%; the selectivity based on DINCH is 98.5%. The cis/trans ratio is 96/4-90/10.

Example 2.5

DOTP Ring Hydrogenation (Dioctyl Terephthalate)

A 300 mL pressure reactor is initially charged with the catalyst A prepared according to Example 1.1. (7.5 g) in a catalyst insert basket, which is admixed with 150 g of dioctyl terephthalate. The hydrogenation was performed with pure hydrogen at a constant pressure of 200 bar and a temperature of 120° C. Hydrogenation is effected for 12 h. The reactor was subsequently decompressed. The conversion is 100%. (GC column: optimal, length 30 m, layer thickness 1 μm; temperature program: 50° C., 10 min, at 10° C./min to 300° C.) The selectivity for dioctyl 1,4-cyclohexanedicarboxylate is 97.7% as a mixture of the cis and trans isomers.

Example 2.6

DOTP (Dioctyl Terephthalate) Ring Hydrogenation with Catalyst C

A 300 mL pressure reactor is initially charged with 10 g of the catalyst C prepared according to Example 1.3 in a catalyst insert basket, which are admixed with 150 g of dioctyl terephthalate. The hydrogenation is performed with pure hydrogen at a constant pressure of 200 bar and a temperature of 120° C. Hydrogenation is effected for 12 h. The reactor is subsequently decompressed. The conversion is 100%. (GC column: optimal, length 30 m, layer thickness 1 μm; temperature program: 50° C., 10 min, at 10° C./min to 300° C.) The selectivity for dioctyl 1,4-cyclohexanedicarboxylate is 97.2% as a mixture of the cis and trans isomers.

Example 2.7

Hydrogenation of Benzoic Acid

A 300 mL pressure reactor is initially charged with 3 g of the catalyst A prepared according to Example 1.1 in a catalyst insert basket, which are admixed with 48 g of benzoic acid dissolved in 72 g of THF (40% by weight). The hydrogenation is performed with pure hydrogen at a constant pressure of 200 bar and a temperature of 150° C. (20 hours). The reactor is subsequently decompressed. The conversion of benzoic acid is 100% (GC column: PB-FFAP, length 25 m, layer thickness 0.25 μm; temperature program: from 40° C. at 5° C./min to 230° C.). The selectivity for cyclohexanecarboxylic acid is 95 area %. Secondary components which can be detected are approx. 5 area % of low boilers (components with a lower boiling point than cyclohexanecarboxylic acid).

Example 2.8

Hydrogenation of 2-methylphenol to 2-methylcyclohexanol

A 300 mL pressure reactor is initially charged with 5 g of the catalyst A prepared according to Example 1.1 in a catalyst insert basket, which are admixed with 180 mL of a 25% solution of ortho-cresol (2-methylphenol) in THF. The hydrogenation is performed with pure hydrogen at a constant pressure of 200 bar and a temperature of 100° C. Hydrogenation is continued until no further hydrogen is taken up (10 hours). The reactor is subsequently decompressed. The conversion of ortho-cresol is 100%. The selectivity for cis/trans-2-methylcyclohexanol is 98.6%. The cis/trans ratio of the 2-methylcyclohexanol obtained is 1.59:1.

Example 2.9

Hydrogenation of Bisphenol A

A 300 mL pressure reactor is initially charged with 3.6 g of the catalyst A prepared according to Example 1.1 in a catalyst insert basket, which are admixed with 100 g of a 30% solution of bisphenol A in n-butanol. The hydrogenation is performed with pure hydrogen at a constant pressure of 200 bar and a temperature of 180° C. Hydrogenation is effected for 24 h. The reactor is subsequently decompressed. The conversion of bisphenol A is 100% (GC column: RTX 65, length 30 m, layer thickness 0.5 μm; temperature program: 280° C., 40 min, isotherm). The selectivity for ring-hydrogenated bisphenol A is 85.77 area %. Secondary components which can be detected are approx. 14.23 area % of low boilers (components with a lower boiling point than ring-hydrogenated bisphenol A).

Example 2.10

Hydrogenation of Cuminaldehyde to Isopropylcyclohexylmethanol

A 300 mL pressure reactor is initially charged with 3.5 g of the catalyst A prepared according to Example 1.1 in a catalyst insert basket, which are admixed with 100 g of cuminaldehyde. The hydrogenation is performed with pure hydrogen at a constant pressure of 200 bar and a temperature of 160° C. Hydrogenation is continued until no further hydrogen is taken up (20 hours). The reactor is subsequently decompressed. The conversion of cuminaldehyde is 100% (GC column: DB-Wax, length 30 m, layer thickness 0.25 μm; temperature program: from 60° C. at 2.5° C./min to 240° C.). The selectivity for isopropylcyclohexylmethanol is 83.2 area %. Secondary components which can be detected are approx. 15 area % of low boilers (components with a lower boiling point than isopropylcyclohexylmethanol).

Example 2.11

Hydrogenation of Cuminaldehyde with Catalyst B

A 300 mL pressure reactor is initially charged with 3.5 g of the catalyst B prepared according to Example 1.2 in a catalyst insert basket, which are admixed with 100 g of cuminaldehyde. The hydrogenation is performed with pure hydrogen at a constant pressure of 200 bar and a temperature of 160° C. Hydrogenation is continued until no further hydrogen is taken up (20 hours). The reactor is subsequently decompressed. The conversion of cuminaldehyde is 100% (GC column: DB-Wax, length 30 m, layer thickness 0.25 µm; temperature program: from 60° C. at 2.5° C./min to 240° C.). The selectivity for isopropylcyclohexylmethanol is 60.6 area %. Secondary components which can be detected are approx. 30.5 area % of low boilers (components with a lower boiling point than isopropylcyclohexylmethanol).

Example 2.12

Hydrogenation of Aniline to Cyclohexylamine

A 300 mL pressure reactor is initially charged with 2.9 g of the catalyst A prepared according to Example 1.1 in a catalyst insert basket, which are admixed with 150 g of a 10% solution of aniline in cyclohexylamine. The hydrogenation is performed with pure hydrogen at a constant pressure of 200 bar and a temperature of 160° C. Hydrogenation is effected for 3 h. The reactor is subsequently decompressed. The conversion of aniline is >99.9% (GC column: RTX-35-amine, length 30 m, layer thickness 1.5 µm; temperature program: from 100° C. at 20° C./min to 280° C., 15 min isothermal).

Example 2.13

Hydrogenation of MDA to Dicycan

A 0.3 L pressure reactor is initially charged with 1.2 g of the catalyst A prepared according to Example 1.1 in a catalyst insert basket, which are admixed with 100 g of a 10% solution of MDA (4,4'-methylenedianiline) in dioxane. The hydrogenation is performed with pure hydrogen at a constant temperature of 200 bar and a temperature of 220° C. Hydrogenation is effected for 10 h. The reactor is subsequently decompressed. The conversion of MDA is 98.4% (GC column: RTX 35, length 30 m, layer thickness 0.5 µm; temperature program: from 100° C. at 5° C./min to 160° C., from 160° C. at 2° C./min to 250° C.). The selectivity for dicycan (4,4'-methylene(diaminocyclohexane) is 88 area %.

Example 2.14

Hydrogenation of Ortho-Toluidine Base to Dimethyldicycan

A 300 mL pressure reactor is initially charged with 1.2 g of the catalyst A prepared according to Example 1.1 in a catalyst insert basket, which are admixed with 160 g of a 12% solution of ortho-toluidine base (2,2'-dimethyl-4,4'-methylenebis (aniline)) in THF. The hydrogenation is performed with pure hydrogen at a constant pressure of 200 bar and a temperature of 220° C. Hydrogenation is effected for 8 h. The reactor is subsequently decompressed. The conversion of o-toluidine base is 100% (GC column: DB-1, length 30 m, layer thickness 1 µm; temperature program: from 150° C. at 8° C./min to 280° C.). The selectivity for dimethyldicycan (2,2'-dimethyl-4,4'-methylenebis(cyclohexylamine)) is 89.1 area %.

Example 2.15

Hydrogenation of Ortho-Toluidine Base to Dimethyldicycan with Catalyst C

A 300 mL pressure reactor is initially charged with 0.8 g of the catalyst C prepared according to Example 1.3 in a catalyst insert basket, which is admixed with 160 g of a 12% solution of ortho-toluidine base (2,2'-dimethyl-4,4'-methylenebis (aniline)) in THF. The hydrogenation is performed with pure hydrogen at a constant pressure of 200 bar and a temperature of 220° C. Hydrogenation is effected for 8 h. The reactor is subsequently decompressed. The conversion of o-toluidine base is 100% (GC column: DB-1, length 30 m, layer thickness 1 µm; temperature program: from 150° C. at 8° C./min to 280° C.). The selectivity for dimethyldicycan (2,2'-dimethyl-4,4'-methylenebis(cyclohexylamine) is 86.8 area %.

Example 2.16

Hydrogenation of Xylidine Base to Tetradimethyldicycan

A 1.2 L pressure reactor is initially charged with 5 g of the catalyst A prepared according to Example 1.1 in a catalyst insert basket, which are admixed with 700 g of a 25% solution of xylidine base (2,2',6,6'-tetramethyl-4,4'-methylenebis (aniline)) in dioxane. The hydrogenation is performed with pure hydrogen at a constant pressure of 200 bar and a temperature of 220° C. Hydrogenation is effected for 2 hours. The reactor is subsequently decompressed. The conversion of xylidine base is 100% (GC column: DB1, length 30 m, layer thickness 0.25 µm; temperature program: from 150° C. at 8° C./min to 280° C.). The selectivity for tetramethyldicycan (2,2',6,6'-tetramethyl-4,4'-methylenebis(cyclohexylamine)) is 89 area %.

Example 2.17

Hydrogenation of Xylidine Base to Tetradimethyldicycan with Catalyst C

A 3.5 L pressure reactor is initially charged with 100 g of the catalyst C prepared according to Example 1.3 in a catalyst insert basket, which are admixed with 2000 g of a 25% solution of xylidine base (2,2',6,6'-tetramethyl-4,4'-methylenebis (aniline)) in THF. The hydrogenation is performed with pure hydrogen at a constant pressure of 200 bar and a temperature of 230° C. Hydrogenation is effected for 2 hours. The reactor is subsequently decompressed. The conversion of xylidine base is 100% (GC column: DB1, length 30 m, layer thickness 0.25 µm; temperature program: from 150° C. at 8° C./min to 280° C.). The mean selectivity from five batches for tetramethyldicycan (2,2',6,6'-tetramethyl-4,4'-methylenebis(cyclohexylamine)) is 76 area %.

Example 2.18

Hydrogenation of Bisphenol A

A 300 mL pressure reactor is initially charged with 3.6 g of the catalyst A prepared according to Example 1.1 in a catalyst insert basket, which are admixed with 100 g of a 30% solution of bisphenol A in n-butanol. The hydrogenation is performed with pure hydrogen at a constant pressure of 200 bar and a temperature of 180° C. Hydrogenation is effected for 16 h. The reactor is subsequently decompressed. The conversion of bisphenol A is 100% (GC column: RTX 65, length 30 m, layer thickness 0.5 μm; temperature program: 280° C., 40 min, isothermal). The selectivity for ring-hydrogenated bisphenol A is 87.5 area %. Secondary components which can be detected are approx. 7.4 area % of low boilers (components with a lower boiling point than ring-hydrogenated bisphenol A).

Example 3

Preparation of Palatinol N (Diisononyl Phatalate)

Process Step 1 (Butene Dimerization):
The butene dimerization is performed continuously in an adiabatic reactor consisting of two component reactors (length: 4 m each, diameter: 80 cm each) with intermediate cooling at 30 bar. The feed material used is a raffinate II with the following composition:
 i-butane: 2% by weight
 n-butane: 10% by weight
 i-butene: 2% by weight
 butene-1: 32% by weight
 butene-2-trans: 37% by weight
 butene-2-cis: 17% by weight
The catalyst used is a material according to DE 4 339 713, consisting of 50% by weight of NiO, 12.5% by weight of $TiO_2$, 33.5% by weight of $SiO_2$ and 4% by weight of $Al_2O_3$ in the form of 5×5 mm tablets. The conversion is performed with a throughput of 0.375 kg of raffinate II/l of catalyst*h, a recycle rate of $C_4$/raffinate II of 3, an inlet temperature in the 1st component reactor of 38° C. and an inlet temperature in the 2nd component reactor of 60° C. The conversion based on the butenes present in the raffinate II is 83.1%; the selectivity for the desired octenes was 83.3%. Fractional distillation of the reactor discharge removes the octene fraction from unconverted raffinate II and the high boilers.

Process Step 2 (Hydroformylation and Subsequent Hydrogenation):
750 g of the octene mixture prepared in process step 1 are reacted batchwise in an autoclave with 0.13% by weight of dicobalt octacarbonyl $Co_2(CO)_8$ as a catalyst with addition of 75 g of water at 185° C. and under a synthesis gas pressure of 280 bar at a mixing ratio of $H_2$ to CO of 60/40 for 5 hours. The consumed synthesis gas, evident from a decline in pressure in the autoclave, is replaced by injecting more. After the decompression of the autoclave, the reaction discharge is freed oxidatively from the cobalt catalyst with 10% by weight of acetic acid by introduction of air, and the organic product phase was hydrogenated with Raney nickel at 125° C. and a hydrogen pressure of 280 bar for 10 h. Fractional distillation of the reaction discharge removes the isononanol fraction from the C8 paraffins and the high boilers.

Process Step 3 (Esterification):
In the third process step, 865.74 g of the isononanol fraction obtained in process step 2 (20% excess based on phthalic anhydride) is reacted with 370.30 g of phthalic anhydride and 0.42 g of isopropyl butyl titanate as a catalyst in a 2 l autoclave with $N_2$ sparging (10 l/h) at a stirrer speed of 500 rpm and a reaction temperature of 230° C. The water of reaction formed is removed continuously from the reaction mixture with the $N_2$ stream. The reaction time is 180 min. Subsequently, the isononanol excess is distilled off under a reduced pressure of 50 mbar. 1000 g of the crude diisononyl phthalate are neutralized with 150 ml of 0.5% sodium hydroxide solution by stirring at 80° C. for 10 minutes. This forms a biphasic mixture with an upper organic phase and a lower aqueous phase (waste liquor comprising hydrolyzed catalyst). The aqueous phase is removed and the organic phase is washed twice with 200 ml of $H_2O$. For further purification, the neutralized and washed diisononyl phthalate is stripped with steam at 180° C. and reduced pressure 50 mbar for 2 h. The purified diisononyl phthalate is then dried at 150° C./50 mbar for 30 min by means of passage of an $N_2$ stream (2 l/h), then stirred with activated carbon for 5 min and filtered with suction through a suction filter with Supra-Theorit 5 filter aid (temperature 80° C.). The diisononyl phthalate thus obtained has a density of 0.973 g/cm$^3$, a viscosity of 73.0 mPa*s, a refractive index $n_D^{20}$ of 1.4853, an acid number of 0.03 mg KOH/g, a water content of 0.03% and a GC purity of 99.83%.

The invention claimed is:

1. An eggshell catalyst comprising an active metal selected from the group consisting of ruthenium, rhodium, palladium, platinum and mixtures thereof, applied to a support material comprising silicon dioxide, wherein the pore volume of the support material is 0.6 to 1.0 ml/g, determined by Hg porosimetry, the BET surface area is 280 to 500 m$^2$/g, and at least 90% of the pores present have a diameter of 6 to 12 nm, and the amount of the active metal is 0.25 to 0.35% by weight, based on the overall eggshell catalyst.

2. The eggshell catalyst according to claim 1, wherein the dispersity of the active metal is 30 to 60%.

3. The eggshell catalyst according to claim 1, wherein the surface area of the active metal is 0.2 to 0.8 m$^2$/g.

4. The eggshell catalyst according to claim 1, which has a tapped density of 400 to 600 g/l.

5. A process for preparing an eggshell catalyst according to claim 1, comprising the steps of:
 (A) impregnating the support material comprising silicon dioxide once or more than once with a solution comprising at least one precursor compound of the active metal,
 (B) then drying,
 (C) then reducing.

6. A process for hydrogenating an organic compound which comprises at least one hydrogenatable group, which comprises contacting the organic compound with at least one reducing agent and an eggshell catalyst according to claim 1.

7. The process according to claim 6, wherein the organic compound to be hydrogenated has at least one carbocyclic aromatic group which is hydrogenated to a corresponding carbocyclic aliphatic group, or has at least one aldehyde group which is hydrogenated to a corresponding alcohol function.

8. The process according to claim 7, wherein the organic compound which has at least one carbocyclic aromatic group is selected from the group consisting of benzene, alkyl-substituted benzenes, phenol, alkyl-substituted phenols, aniline, alkyl-substituted aniline, N,N-dialkylaniline, diaminobenzene, bis(p-aminophenyl)methane, bis(p-aminotolyl)methane, aromatic carboxylic acids, aromatic carboxylic esters and mixtures thereof.

9. The process according to claim 7, wherein the organic compound which is to be hydrogenated and has an aldehyde group is a mono- or disaccharide which is hydrogenated to the corresponding sugar alcohol.

10. The process according to claim 6, wherein the hydrogenation is effected in a fixed bed reactor.

* * * * *